United States Patent
Adamou et al.

(12) United States Patent (10) Patent No.: US 7,132,107 B2
(45) Date of Patent: Nov. 7, 2006

(54) STREPTOCOCCUS PNEUMONIAE PROTEINS AND VACCINES

(75) Inventors: John E. Adamou, Rockville, MD (US); Gil H. Choi, Rockville, MD (US)

(73) Assignees: MedImmune, Inc., Gaithersburg, MD (US); Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/067,385

(22) Filed: Feb. 5, 2002

(65) Prior Publication Data

US 2002/0110562 A1   Aug. 15, 2002

Related U.S. Application Data

(62) Division of application No. 09/590,991, filed on Jun. 9, 2000, now Pat. No. 6,887,480.

(60) Provisional application No. 60/138,453, filed on Jun. 10, 1999.

(51) Int. Cl.
 A61K 39/09   (2006.01)
 A61K 39/02   (2006.01)
 A61K 39/00   (2006.01)
 A61K 38/00   (2006.01)
 C07K 1/00    (2006.01)
 C07K 2/00    (2006.01)

(52) U.S. Cl. .............. 424/244.1; 424/234.1; 424/190.1; 424/184.1; 424/185.1; 514/2; 530/350; 530/300; 530/825

(58) Field of Classification Search ............ 530/350, 530/300, 825; 424/234.1, 184.1, 244.1, 190.1, 424/185.1; 514/2
See application file for complete search history.

(56) References Cited

U.S. PATENT DOCUMENTS

2003/0134407 A1* 7/2003 Le Page et al. ......... 435/252.3

FOREIGN PATENT DOCUMENTS

WO   WO 98/18930   5/1998
WO   WO 00/06738   2/2000

OTHER PUBLICATIONS

Houghten et al. Vaccines86, Cold Spring Harbor Laboratory, p. 21-25, 1986.*
Harlow et al. In: Antibodies: A Laboratory Manual. Cold Spring Harbor Laboratory, Chapter 5, p. 76, 1988.*
Nayak et al., Infection and Immunity, 66:3744-3751 (1998).
Lazar et al., Mol. Cellular Biol. 8:1247-1252 (1988).
Burgess et al., J. Cell. Biol. 111:2129-2138 (1990).
Bowie et al., Science 247:1306-1310 (1990).

* cited by examiner

*Primary Examiner*—S. Devi
(74) *Attorney, Agent, or Firm*—Elliot M. Olstein; Alan J. Grant (57) ABSTRACT

The present invention relates to novel immunogenic polypeptides, and fragments thereof, and vaccines for the prevention and treatment of pneumococcal infection, especially by *Streptococcus pneumoniae*. The invention also relates to antibodies against the disclosed polypeptides, as well as vaccines containing said polypeptides and methods of disease prevention.

6 Claims, 4 Drawing Sheets

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Forward
      primer for PCR amplification of Sp128 genomic sequences

<400> SEQUENCE: 1
tacccggtag tcttagcaga c                                            21

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Reverse
      primer for PCR amplification of Sp128 genomic sequence

<400> SEQUENCE: 2
atagccataa gttgatttgc catta                                        25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Forward
      primer for PCR amplification of Sp130 genomic sequence

<400> SEQUENCE: 3
aagcttggcg agattgcaga a                                            21
```

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Reverse
      primer for PCR amplification of Sp130 genomic sequence

<400> SEQUENCE: 4
cttattagga ttgttagtag ttgattt                                27

<210> SEQ ID NO 5
<211> LENGTH: 1992
<212> TYPE: DNA
<213> ORGANISM: Streptococcus pneumoniae

<400> SEQUENCE: 5
tacccggtag tcttagcaga cacatctagc tctgaagatg ctttaaacat ctctgataaa    60 gaaaagtag cagaaaataa agagaaacat gaaaatatcc atagtgctat ggaaacttca   120 caggattta aagagaagaa aacagcagtc attaaggaaa agaagttgt tagtaaaaat    180 cctgtgatag acaataacac tagcaatgaa gaagcaaaaa tcaaagaaga aaattccaat   240
aaatcccaag gagattatac ggactcattt gtgaataaaa acacagaaaa tcccaaaaaa   300
gaagataaag ttgtctatat tgctgaattt aaagataaag aatctggaga aaaagcaatc   360
aaggaactat ccagtcttaa gaatacaaaa gtttttatata cttatgatag aattttttaac   420 ggtagtgcca tagaaacaac tccagataac ttggacaaaa ttaaacaaat agaaggtatt   480
tcatcggttg aaagggcaca aaaagtccaa cccatgatga atcatgccag aaaggaaatt   540
ggagttgagg aagctattga ttacctaaag tctatcaatg ctccgtttgg gaaaaatttt   600
gatggtagag gtatggtcat ttcaaatatc gatactggaa cagattatag acataaggct   660
atgagaatcg atgatgatgc caaagcctca atgagattta aaaagaaga cttaaaaggc   720 actgataaaa attattggtt gagtgataaa atccctcatg cgttcaatta ttataatggt   780
ggcaaaatca ctgtagaaaa atatgatgat ggaagggatt attttgaccc acatgggatg   840
catattgcag ggattcttgc tggaaatgat actgaacaag acatcaaaaa ctttaacggc   900
atagatggaa ttgcacctaa tgcacaaatt ttctcttaca aaatgtattc tgacgcagga   960
tctgggtttg cgggtgatga acaatgtttt catgctattg aagattctat caaacacaac  1020
gttgatgttg tttcggtatc atctggtttt acaggaacag gtcttgtagg tgagaaatat  1080
tggcaagcta ttcgggcatt aagaaaagca ggcattccaa tggttgtcgc tacgggtaac  1140
tatgcgactt ctgcttcaag ttcttcatgg gatttagtag caaataatca tctgaaaatg  1200
accgacactg gaaatgtaac acgaactgca gcacatgaag atgcgatagc ggtcgcttct  1260
gctaaaaatc aaacagttga gtttgataaa gttaacatag gtgagaaag ttttaaatac   1320 agaaatatag gggcctttt cgataagagt aaaatcacaa caaatgaaga tggaacaaaa  1380
gctcctagta aattaaaatt tgtatatata ggcaaggggc aagaccaaga tttgataggt  1440
ttggatctta ggggcaaaat tgcagtaatg gatagaattt atacaaagga tttaaaaaat  1500
gcttttaaaa aagctatgga taaggtgca cgcgccatta tggttgtaaa tactgtaaat  1560
tactacaata gagataattg gacagagctt ccagctatgg gatatgaagc ggatgaaggt  1620 actaaagtc aagtgttttc aatttcagga gatgatggtg taaagctatg gaacatgatt  1680
aatcctgata aaaaaactga agtcaaaaga aataataaag aagattttaa agataaattg  1740

-continued

```
gagcaatact atccaattga tatggaaagt tttaattcca acaaaccgaa tgtaggtgac      1800
gaaaaagaga ttgactttaa gtttgcacct gacacagaca aagaactcta taaagaagat      1860
atcatcgttc cagcaggatc tacatcttgg gggccaagaa tagatttact tttaaaaccc      1920
gatgtttcag cacctggtaa aaatattaaa tccacgctta atgttattaa tggcaaatca      1980
acttatggct at                                                          1992
```

<210> SEQ ID NO 6
<211> LENGTH: 664
<212> TYPE: PRT
<213> ORGANISM: Streptococcus pneumoniae

<400> SEQUENCE: 6

```
Tyr Pro Val Val Leu Ala Asp Thr Ser Ser Glu Asp Ala Leu Asn
 1               5                  10                  15

Ile Ser Asp Lys Glu Lys Val Ala Glu Asn Lys Glu Lys His Glu Asn
                20                  25                  30

Ile His Ser Ala Met Glu Thr Ser Gln Asp Phe Lys Glu Lys Lys Thr
            35                  40                  45

Ala Val Ile Lys Glu Lys Glu Val Ser Lys Asn Pro Val Ile Asp
     50                  55                  60

Asn Asn Thr Ser Asn Glu Glu Ala Lys Ile Lys Glu Glu Asn Ser Asn
 65                  70                  75                  80

Lys Ser Gln Gly Asp Tyr Thr Asp Ser Phe Val Asn Lys Asn Thr Glu
                85                  90                  95

Asn Pro Lys Lys Glu Asp Lys Val Val Tyr Ile Ala Glu Phe Lys Asp
            100                 105                 110

Lys Glu Ser Gly Glu Lys Ala Ile Lys Glu Leu Ser Ser Leu Lys Asn
        115                 120                 125

Thr Lys Val Leu Tyr Thr Tyr Asp Arg Ile Phe Asn Gly Ser Ala Ile
    130                 135                 140

Glu Thr Thr Pro Asp Asn Leu Asp Lys Ile Lys Gln Ile Glu Gly Ile
145                 150                 155                 160

Ser Ser Val Glu Arg Ala Gln Lys Val Gln Pro Met Met Asn His Ala
                165                 170                 175

Arg Lys Glu Ile Gly Val Glu Glu Ala Ile Asp Tyr Leu Lys Ser Ile
            180                 185                 190

Asn Ala Pro Phe Gly Lys Asn Phe Asp Gly Arg Gly Met Val Ile Ser
        195                 200                 205

Asn Ile Asp Thr Gly Thr Asp Tyr Arg His Lys Ala Met Arg Ile Asp
    210                 215                 220

Asp Asp Ala Lys Ala Ser Met Arg Phe Lys Lys Glu Asp Leu Lys Gly
225                 230                 235                 240

Thr Asp Lys Asn Tyr Trp Leu Ser Asp Lys Ile Pro His Ala Phe Asn
                245                 250                 255

Tyr Tyr Asn Gly Gly Lys Ile Thr Val Glu Lys Tyr Asp Asp Gly Arg
            260                 265                 270

Asp Tyr Phe Asp Pro His Gly Met His Ile Ala Gly Ile Leu Ala Gly
        275                 280                 285

Asn Asp Thr Glu Gln Asp Ile Lys Asn Phe Asn Gly Ile Asp Gly Ile
    290                 295                 300

Ala Pro Asn Ala Gln Ile Phe Ser Tyr Lys Met Tyr Ser Asp Ala Gly
305                 310                 315                 320
```

```
Ser Gly Phe Ala Gly Asp Glu Thr Met Phe His Ala Ile Glu Asp Ser
            325                 330                 335

Ile Lys His Asn Val Asp Val Val Ser Val Ser Ser Gly Phe Thr Gly
            340                 345                 350

Thr Gly Leu Val Gly Glu Lys Tyr Trp Gln Ala Ile Arg Ala Leu Arg
            355                 360                 365

Lys Ala Gly Ile Pro Met Val Val Ala Thr Gly Asn Tyr Ala Thr Ser
            370                 375                 380

Ala Ser Ser Ser Ser Trp Asp Leu Val Ala Asn Asn His Leu Lys Met
385                 390                 395                 400

Thr Asp Thr Gly Asn Val Thr Arg Thr Ala Ala His Glu Asp Ala Ile
            405                 410                 415

Ala Val Ala Ser Ala Lys Asn Gln Thr Val Glu Phe Asp Lys Val Asn
            420                 425                 430

Ile Gly Gly Glu Ser Phe Lys Tyr Arg Asn Ile Gly Ala Phe Phe Asp
            435                 440                 445

Lys Ser Lys Ile Thr Thr Asn Glu Asp Gly Thr Lys Ala Pro Ser Lys
            450                 455                 460

Leu Lys Phe Val Tyr Ile Gly Lys Gly Gln Asp Gln Leu Ile Gly
465                 470                 475                 480

Leu Asp Leu Arg Gly Lys Ile Ala Val Met Asp Arg Ile Tyr Thr Lys
            485                 490                 495

Asp Leu Lys Asn Ala Phe Lys Lys Ala Met Asp Lys Gly Ala Arg Ala
            500                 505                 510

Ile Met Val Val Asn Thr Val Asn Tyr Tyr Asn Arg Asp Asn Trp Thr
            515                 520                 525

Glu Leu Pro Ala Met Gly Tyr Glu Ala Asp Gly Thr Lys Ser Gln
            530                 535                 540

Val Phe Ser Ile Ser Gly Asp Asp Gly Val Lys Leu Trp Asn Met Ile
545                 550                 555                 560

Asn Pro Asp Lys Lys Thr Glu Val Lys Arg Asn Asn Lys Glu Asp Phe
            565                 570                 575

Lys Asp Lys Leu Glu Gln Tyr Tyr Pro Ile Asp Met Glu Ser Phe Asn
            580                 585                 590

Ser Asn Lys Pro Asn Val Gly Asp Glu Lys Glu Ile Asp Phe Lys Phe
            595                 600                 605

Ala Pro Asp Thr Asp Lys Glu Leu Tyr Lys Glu Asp Ile Ile Val Pro
            610                 615                 620

Ala Gly Ser Thr Ser Trp Gly Pro Arg Ile Asp Leu Leu Leu Lys Pro
625                 630                 635                 640

Asp Val Ser Ala Pro Gly Lys Asn Ile Lys Ser Thr Leu Asn Val Ile
            645                 650                 655

Asn Gly Lys Ser Thr Tyr Gly Tyr
            660

<210> SEQ ID NO 7
<211> LENGTH: 2319
<212> TYPE: DNA
<213> ORGANISM: Streptococcus pneumoniae

<400> SEQUENCE: 7
aagcttggcg agattgcaga atctaaattt aaaaatttag gaaatggaaa agagggtagt      60
ctaaaaaaag atacaactgg ggtagaacat catcatcaag aaaatgaaga gtctattaaa     120
gaaaaatcta gttttactat tgatagaaat atttcaacaa ttagagactt tgaaaataaa     180
```

-continued

```
gacttaaaga aactcattaa aaagaaattt agagaagttg atgattttac aagtgaaact    240
ggtaagagaa tggaggaata cgattataaa tacgatgata aaggaaatat aatagcctac    300
gatgatggga ctgatctaga atatgaaact gagaaacttg acgaaatcaa atcaaaaatt    360
tatggtgttc taagtccgtc taaagatgga cactttgaaa ttcttggaaa gataagtaat    420
gtttctaaaa atgccaaggt atattatggg aataactata atctataga atcaaagcg     480 accaagtatg atttccactc aaaaacgatg acatttgatc tatacgctaa tattaatgat    540
attgtggatg gattagcttt tgcaggagat atgagattat tgttaaaga taatgatcag     600 aaaaaagctg aaattaaaat tagaatgcct gaaaaaatta aggaaactaa atcagaatat    660
ccctatgtat caagttatgg gaatgtcata gaattagggg aaggagatct ttcaaaaaac    720
aaaccagaca atttaactaa aatggaatct ggtaaaatct attctgattc agaaaaacaa    780
caatatctgt taaggataa tatcattcta agaaaaggct atgcactaaa agtgactacc     840
tataatcctg aaaaacgga tatgttagaa ggaaatggag tctatagcaa ggaagatata    900
gcaaaaatac aaaaggccaa tcctaatcta agagcccttt cagaaacaac aatttatgct    960
gatagtagaa atgttgaaga tggaagaagt acccaatctg tattaatgtc ggctttggac   1020
ggctttaaca ttataaggta tcaagtgttt acatttaaaa tgaacgataa aggggaagct   1080
atcgataaag acggaaatct tgtgacagat tcttctaaac ttgtattatt tggtaaggat   1140
gataaagaat acactggaga ggataagttc aatgtagaag ctataaaaga agatggctcc   1200 atgttatttta ttgataccaa accagtaaac ctttcaatgg ataagaacta ctttaatcca   1260
tctaaatcta ataaaattta tgtacgaaat ccagaatttt atttaagagg taagatttct   1320
gataagggtg gttttaactg ggaattgaga gttaatgaat cggttgtaga taattattta   1380
atctacggag atttacacat tgataacact agagatttta atattaagct gaatgttaaa   1440
gacggtgaca tcatggactg gggaatgaaa gactataaag caaacggatt tccagataag   1500
gtaacagata tggatggaaa tgtttatctt caaactggct atagcgattt gaatgctaaa   1560
gcagttggag tccactatca gtttttatat gataatgtta aacccgaagt aaacattgat   1620
cctaagggaa atactagtat cgaatatgct gatggaaaat ctgtagtctt taacatcaat   1680
gataaaagaa ataatggatt cgatggtgag attcaagaac aacatattta tataaatgga   1740
aagaatatat catcatttaa tgatattaaa caaataatag acaagacact aaacattaag   1800
attgttgtaa aagattttgc aagaaataca accgtaaaag aattcatttt aaataaagat   1860
acgggagagg taagtgaatt aaaaacctcat agggtaactg tgaccattca aaatggaaaa   1920
gaaatgagtt caacgatagt gtcggaagaa gattttattt tacctgttta taagggtgaa   1980
ttagaaaaag gataccaatt tgatggttgg gaaatttctg gtttcgaagg taaaaaagac   2040
gctggctatg ttattaatct atcaaaagat acctttataa aacctgtatt caagaaaata   2100
gaggagaaaa aggaggaaga aaataaacct acttttgatg tatcgaaaaa gaaagataac   2160
ccacaagtaa accatagtca attaaatgaa agtcacagaa aagaggattt acaaagagaa   2220
gagcattcac aaaaatctga ttcaactaag gatgttacag ctacagttct tgataaaaac   2280
aatatcagta gtaaatcaac tactaacaat cctaataag                           2319
```

<210> SEQ ID NO 8
<211> LENGTH: 773
<212> TYPE: PRT
<213> ORGANISM: Streptococcus pneumoniae -continued

<400> SEQUENCE: 8

```
Lys Leu Gly Glu Ile Ala Glu Ser Lys Phe Lys Asn Leu Gly Asn Gly
  1               5                  10                  15

Lys Glu Gly Ser Leu Lys Lys Asp Thr Thr Gly Val Glu His His His
             20                  25                  30

Gln Glu Asn Glu Glu Ser Ile Lys Glu Lys Ser Ser Phe Thr Ile Asp
         35                  40                  45

Arg Asn Ile Ser Thr Ile Arg Asp Phe Glu Asn Lys Asp Leu Lys Lys
     50                  55                  60

Leu Ile Lys Lys Lys Phe Arg Glu Val Asp Asp Phe Thr Ser Glu Thr
 65                  70                  75                  80

Gly Lys Arg Met Glu Glu Tyr Asp Tyr Lys Tyr Asp Asp Lys Gly Asn
                 85                  90                  95

Ile Ile Ala Tyr Asp Asp Gly Thr Asp Leu Glu Tyr Glu Thr Glu Lys
            100                 105                 110

Leu Asp Glu Ile Lys Ser Lys Ile Tyr Gly Val Leu Ser Pro Ser Lys
            115                 120                 125

Asp Gly His Phe Glu Ile Leu Gly Lys Ile Ser Asn Val Ser Lys Asn
        130                 135                 140

Ala Lys Val Tyr Tyr Gly Asn Asn Tyr Lys Ser Ile Glu Ile Lys Ala
145                 150                 155                 160

Thr Lys Tyr Asp Phe His Ser Lys Thr Met Thr Phe Asp Leu Tyr Ala
                165                 170                 175

Asn Ile Asn Asp Ile Val Asp Gly Leu Ala Phe Ala Gly Asp Met Arg
            180                 185                 190

Leu Phe Val Lys Asp Asn Asp Gln Lys Lys Ala Glu Ile Lys Ile Arg
        195                 200                 205

Met Pro Glu Lys Ile Lys Glu Thr Lys Ser Glu Tyr Pro Tyr Val Ser
    210                 215                 220

Ser Tyr Gly Asn Val Ile Glu Leu Gly Glu Gly Asp Leu Ser Lys Asn
225                 230                 235                 240

Lys Pro Asp Asn Leu Thr Lys Met Glu Ser Gly Lys Ile Tyr Ser Asp
                245                 250                 255

Ser Glu Lys Gln Gln Tyr Leu Leu Lys Asp Asn Ile Ile Leu Arg Lys
            260                 265                 270

Gly Tyr Ala Leu Lys Val Thr Thr Tyr Asn Pro Gly Lys Thr Asp Met
        275                 280                 285

Leu Glu Gly Asn Gly Val Tyr Ser Lys Glu Asp Ile Ala Lys Ile Gln
    290                 295                 300

Lys Ala Asn Pro Asn Leu Arg Ala Leu Ser Glu Thr Thr Ile Tyr Ala
305                 310                 315                 320

Asp Ser Arg Asn Val Glu Asp Gly Arg Ser Thr Gln Ser Val Leu Met
                325                 330                 335

Ser Ala Leu Asp Gly Phe Asn Ile Ile Arg Tyr Gln Val Phe Thr Phe
            340                 345                 350

Lys Met Asn Asp Lys Gly Glu Ala Ile Asp Lys Asp Gly Asn Leu Val
        355                 360                 365

Thr Asp Ser Ser Lys Leu Val Leu Phe Gly Lys Asp Lys Glu Tyr
    370                 375                 380

Thr Gly Glu Asp Lys Phe Asn Val Glu Ala Ile Lys Glu Asp Gly Ser
385                 390                 395                 400

Met Leu Phe Ile Asp Thr Lys Pro Val Asn Leu Ser Met Asp Lys Asn
                405                 410                 415
```

```
Tyr Phe Asn Pro Ser Lys Ser Asn Lys Ile Tyr Val Arg Asn Pro Glu
            420                 425                 430

Phe Tyr Leu Arg Gly Lys Ile Ser Asp Lys Gly Gly Phe Asn Trp Glu
            435                 440                 445

Leu Arg Val Asn Glu Ser Val Val Asp Asn Tyr Leu Ile Tyr Gly Asp
            450                 455                 460

Leu His Ile Asp Asn Thr Arg Asp Phe Asn Ile Lys Leu Asn Val Lys
465                 470                 475                 480

Asp Gly Asp Ile Met Asp Trp Gly Met Lys Asp Tyr Lys Ala Asn Gly
                    485                 490                 495

Phe Pro Asp Lys Val Thr Asp Met Asp Gly Asn Val Tyr Leu Gln Thr
            500                 505                 510

Gly Tyr Ser Asp Leu Asn Ala Lys Ala Val Gly Val His Tyr Gln Phe
            515                 520                 525

Leu Tyr Asp Asn Val Lys Pro Glu Val Asn Ile Asp Pro Lys Gly Asn
            530                 535                 540

Thr Ser Ile Glu Tyr Ala Asp Gly Lys Ser Val Val Phe Asn Ile Asn
545                 550                 555                 560

Asp Lys Arg Asn Asn Gly Phe Asp Gly Glu Ile Gln Glu Gln His Ile
                565                 570                 575

Tyr Ile Asn Gly Lys Glu Tyr Thr Ser Phe Asn Asp Ile Lys Gln Ile
                580                 585                 590

Ile Asp Lys Thr Leu Asn Ile Lys Ile Val Lys Asp Phe Ala Arg
                595                 600                 605

Asn Thr Thr Val Lys Glu Phe Ile Leu Asn Lys Asp Thr Gly Glu Val
            610                 615                 620

Ser Glu Leu Lys Pro His Arg Val Thr Val Thr Ile Gln Asn Gly Lys
625                 630                 635                 640

Glu Met Ser Ser Thr Ile Val Ser Glu Glu Asp Phe Ile Leu Pro Val
                645                 650                 655

Tyr Lys Gly Glu Leu Glu Lys Gly Tyr Gln Phe Asp Gly Trp Glu Ile
            660                 665                 670

Ser Gly Phe Glu Gly Lys Lys Asp Ala Gly Tyr Val Ile Asn Leu Ser
            675                 680                 685

Lys Asp Thr Phe Ile Lys Pro Val Phe Lys Lys Ile Glu Glu Lys Lys
            690                 695                 700

Glu Glu Glu Asn Lys Pro Thr Phe Asp Val Ser Lys Lys Lys Asp Asn
705                 710                 715                 720

Pro Gln Val Asn His Ser Gln Leu Asn Glu Ser His Arg Lys Glu Asp
                725                 730                 735

Leu Gln Arg Glu Glu His Ser Gln Lys Ser Asp Ser Thr Lys Asp Val
            740                 745                 750

Thr Ala Thr Val Leu Asp Lys Asn Ile Ser Ser Lys Ser Thr Thr
            755                 760                 765

Asn Asn Pro Asn Lys
            770
```

STREPTOCOCCUS PNEUMONIAE PROTEINS AND VACCINES

This application is a Divisional of application Ser. No. 09/590,991, filed Jun. 9, 2000, now U.S. Pat. No. 6,887,480, which claims priority to the U.S. provisional application No. 60/138,453, filed Jun. 10, 1999, the disclosure of which is hereby incorporated by reference in its entirety.

BACKGROUND OF THE INVENTION

*Streptococcus pneumoniae* is a gram positive bacterium which is a major causative agent in invasive infections in animals and humans, such as sepsis, meningitis, otitis media and lobar pneumonia (Tuomanen, et al. NEJM 322:1280–1284 (1995)). As part of the infective process, pneumococci readily bind to non-inflamed human epithelial cells of the upper and lower respiratory tract by binding to eukaryotic carbohydrates in a lectin-like manner (Cundell et al., Micro. Path. 17:361–374 (1994)). Conversion to invasive pneumococcal infections for bound bacteria may involve the local generation of inflammatory factors which may activate the epithelial cells to change the number and type of receptors on their surface (Cundell, et al., Nature, 377:435–438 (1995)). Apparently, one such receptor, platelet activating factor (PAF) is engaged by the pneumococcal bacteria and within a very short period of time (minutes) from the appearance of PAF, pneumococci exhibit strongly enhanced adherence and invasion of tissue. Certain soluble receptor analogs have been shown to prevent the progression of pneumococcal infections (Idanpaan-Heikkila et al., J. Inf. Dis., 176:704–712 (1997)). A number of various other proteins have been suggested as being involved in the pathogenicity of *S. pneumoniae* but only some have been confirmed as virulence factors. Despite the fact that there are capsule conjugates currently in trial, there still remains a need for identifying additional polypeptides having epitopes in common from various strains of *S. pneumoniae* in order to utilize such polypeptides as vaccines to provide protection against a wide variety of *S. pneumoniae* serotypes.

BRIEF SUMMARY OF THE INVENTION

The invention disclosed herein relates to vaccines derived from polypeptides of the pneumococcal organism *Streptococcus pneumoniae*. In accordance with the present invention there are disclosed herein several protein sequences, and fragments thereof and their corresponding nucleotide sequences used for recombinantly preparing said polypeptides.

More specifically, the present invention discloses 2 large polypeptides, one denoted Sp128 (SEQ ID NO:6), composed of 664 amino acid residues, and a second polypeptide, denoted Sp130, containing 773 amino acid residues (SEQ ID NO:8). Both Sp128 and Sp130 have been found to confer protective properties on animals immunized with said polypeptides, or portions thereof.

The present invention also relates to the field of bacterial antigens and their use, for example, as immunogenic agents in humans and animals to stimulate an immune response. More specifically, it relates to the vaccination of mammalian species with one or more recombinant polypeptides produced according to the invention disclosed herein, such recombinant polypeptides being derived from *Streptococcus pneumoniae*.

In accordance with the present invention, such proteins serve as a mechanism for stimulating production of antibodies that protect the vaccine recipient against infection by a wide range of capsular serotypes of pathogenic *S. pneumoniae*.

The invention disclosed herein further relates to antisera and antibodies against such polypeptides useful in diagnosis and passive immune therapy with respect to diagnosing and treating such pneumococcal infections. Like the vaccines disclosed herein, the antibodies specific for such antigenic polypeptides, and fragments thereof, can be prepared recombinantly by transforming cells with vectors containing the appropriate gene sequences to produce the active tetrameric antibody. Such methods are well known in the art.

In a particular aspect, the present invention relates to the prevention and treatment of pneumococcal infections such as infections of the middle ear, nasopharynx, lung and bronchial areas, blood, CSF, and the like, that are caused by pneumococcal bacteria.

The present invention further relates to vaccines prepared from the novel proteins and polypeptides, as well as fragments and segments thereof, disclosed herein. In addition, examples of the use of such proteins and polypeptides as vaccines for the protection of mammals are likewise disclosed.

BRIEF DESCRIPTION OF THE DRAWINGS

FIG. 1 shows the results of 2 experiments (FIGS. 1A and 1B, respectively), using the same preparations of Sp128 and Sp130 polypeptides. The results demonstrate that active immunization with recombinant Sp128 or Sp130 polypeptides derived from the pneumococcal strain Norway serotype 4 is able to protect mice from death in a model of pneumococcal sepsis using the heterologous strain SJ2 (serotype 6B). In these 2 experiments, 90% and 100%, respectively, of the mice immunized with Sp130 survived the 14 day observation period following challenge with about 400 CFU (colony forming units) of pneumococci. Conversely, 100% of sham immunized mice (injected only with PBS (phosphate-buffered saline) plus adjuvant) died during the same period. In addition, for both experiments, 90% of the mice immunized with Sp128 survived the same 14 day observation period.

FIG. 4A shows the results for Sp128. FIG. 4B shows the results for Sp130. The recombinant proteins were resolved by SDS-PAGE and transferred to nitrocellulose. Sera were collected from 5 patients (indicated by number at the top) at two different times. First collection (denoted "A" for "acute serum") was soon after onset of illness; second collection (denoted "C" for "convalescent") was made 8 to 30 days later. These sera were used to probe the blots. The results show that for patients 2, 3 and 5, convalescent serum reacted more strongly with Sp128 and Sp130 than did the corresponding acute serum. Such findings constitute indirect evidence that both Sp128 and Sp130 are expressed by *S. pneumoniae* during this phase of infection.

DETAILED SUMMARY OF THE INVENTION

In accordance with the present invention there is disclosed herein recombinant polypeptides corresponding to Sp128 (SEQ ID NO: 6) and Sp130 (SEQ ID NO: 8).

It is an object of the present invention to provide methods of utilizing these recombinant polypeptides, and immunogenically active fragments thereof, as a means of immunizing animals, especially mammals, most especially humans, against a variety of microbial infections, especially pneumococcal infections.

It is a further object of the present invention to provide polypeptides, as disclosed herein, and active fragments thereof, whether derived from natural sources or prepared by means of recombinant technology, for use in immunizing animals, especially mammals, most especially humans, against pneumococcal infection.

It is a still further object of the present invention to provide vaccines that include polypeptides obtained from *S. pneumoniae* and/or variants of said polypeptides and/or active fragments of such polypeptides, including polypeptides prepared by recombinant means (i.e., recombinant polypeptides and proteins).

In accordance with the present invention, there are also disclosed herein nucleic acids and DNA sequences and molecules, and fragments thereof (and their corresponding isolated RNA sequences, and molecules and fragments thereof) showing sequence homology with, or identity to, or capable of hybridizing to, the DNA sequences identified in SEQ ID NOS: 5 and 7. The present invention also relates to DNA (or RNA) sequences encoding the same polypeptide as is encoded by the sequences of SEQ ID NOS: 5 and 7, including fragments and portions thereof and, when derived from natural sources, including alleles thereof, for the express purpose of facilitating the recombinant expression of the immunogenic polypeptides, and immunogenic fragments thereof, disclosed herein.

Thus, an isolated DNA (or RNA) sequence can include only the coding region of the expressed gene (or fragment or portion thereof as hereinabove indicated) or can further include all or a portion of the non-coding DNA (or RNA) of the expressed human gene.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[1-(C/R)]$ wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

In accordance with the present invention, there are disclosed herein the polynucleotide sequences coding for the polypeptide vaccines of the invention so as to facilitate recombinant expression of said polypeptides. Such polynucleotides code for the polypeptides of SEQ ID NOS: 6 and 8 and are disclosed as the sequences of SEQ ID NOS: 5 and 7.

For purposes of recombinantly expressing the polypeptide vaccines of the invention, the polynucleotides of SEQ ID NOS: 5 and 7 may also have the coding sequence fused in frame to a marker sequence which allows for purification of the polypeptide of the present invention. The marker sequence may be a hexa-histidine tag (for example, as can be supplied by a pQE-9 vector) to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

To facilitate generation of the polynucleotides disclosed herein, appropriate PCR primers are provided as SEQ ID NOS: 1 (5'-primer for Sp128), 2 (3'-primer for Sp128), 3 (5'-primer for Sp130), and 4 (3'-primer for Sp130).

The polypeptides, and fragments thereof, of the vaccines disclosed as expression products according to the invention may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

"Isolated" in the context of the present invention with respect to polypeptides means that the material is removed from its original environment (e.g., the natural environment if it is naturally occurring). For example, a naturally-occurring polynucleotide or polypeptide present in a living organism is not isolated, but the same polypeptide, separated from some or all of the co-existing materials in the natural system, is isolated. Such polypeptides could be part of a composition, and still be isolated in that such composition is not part of its natural environment. The polypeptides of the vaccines disclosed herein are preferably provided in an isolated form, and preferably are purified to homogeneity.

The recombinant or immunogenic polypeptides disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, claimed polypeptide which has a purity of preferably 0.001%, or at least 0.01% or 0.1%; and even desirably 1% by weight or greater is expressly contemplated.

The term "coding region" refers to that portion of a gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

The term "primer" means a short nucleic acid sequence that is paired with one strand of DNA and provides a free 3'OH end at which a DNA polymerase starts synthesis of a deoxyribonucleotide chain.

At the simplest level, the amino acid sequence corresponding to all or part of the polypeptides according to the present invention can be synthesized using commercially available peptide synthesizers. This is particularly useful in producing small peptides and fragments of larger polypeptides. (Fragments are useful, for example, in generating antibodies against the native polypeptide.)

The terms "fragment," "derivative" and "analog," when referring to the polypeptides according to the present invention, means a polypeptide which retains essentially the same biological function or activity as said polypeptide. Thus, an analog includes a proprotein which can be activated by cleavage of the proprotein portion to produce an active mature polypeptide. Such fragments, derivatives and analogs must have sufficient similarity to the polypeptides SEQ ID NOS: 6 and 8, so that activity of the native polypeptide is retained.

The polypeptide vaccines of the present invention may be recombinant polypeptides, natural polypeptides or synthetic polypeptides, preferably recombinant polypeptides.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., *E. coli*, will be free of glycosylation modifications that might normally accur in yeast or mammalian expression systems. Thus, the patterns of such post-translational modifications will differ with the expression system. However, all such variants are considered to lie within the disclosure of the present invention.

A vaccine according to the present invention would include a polypeptide, including immunogenic fragments thereof, comprising an amino acid sequence at least 65% identical, preferably 80% identical, most preferably 95% identical and ideally 100% identical to the amino acid sequence of SEQ ID NO:6.

Such vaccines would also comprise a polypeptide, including immunogenic fragments thereof, having an amino acid sequence at least 65% identical, preferably 80% identical, most preferably 95% identical, and ideally 100% identical to the amino acid sequence of SEQ ID NO:8.

The present invention is also directed to an antiserum produced by immunizing an animal with a polypeptide according to the invention. The invention also includes an isolated antibody that binds specifically to a polypeptide of the invention. Such an antibody may be a monoclonal antibody, possibly produced by a hybridoma cell line, and may also include a recombinantly produced antibody formed by introducing into a suitable cell line the gene sequences required for producing an antibody specific for the polypeptide vaccines disclosed herein.

The present invention is also directed to a vaccine comprising one or more *S. pneumoniae* polypeptides selected from the polypeptides, and immunogenic fragments thereof, disclosed herein, suspended in a pharmaceutically acceptable diluent, carrier or excipient, provided that said polypeptide is present in an amount effective to elicit protective antibodies in an animal against an organism related to the genus Streptococcus, preferably an organism of the genus Streptococcus, and most preferably where the organism is *Streptococcus pneumoniae*.

The present invention also provides for a method of preventing or treating an infection caused by a member of the genus Streptococcus in an animal, comprising administering to an animal, especially a mammal, and most especially a human being, a polypeptide, or immunogenic fragment thereof, as disclosed herein, and wherein said polypeptide, or immunogenic fragment thereof, is administered in an amount effective to prevent or attenuate said infection. In using the methods of the invention, the disease to be prevented or treated will preferably be a pneumococcal infection, most preferably an infection by an organism that is a member of the genus *Streptococcus*, ideally *Streptococcus pneumoniae*.

A vaccine disclosed according to the present invention may also include a vaccine comprising a microbial organism transformed with polynucleotides, and thereby expressing the polypeptides, or fragments thereof, selected from the group consisting of Sp128 and Sp130 (SEQ ID NOS: 6 and 8, respectively). The present invention would thus also encompass a method of preventing or attenuating an infection caused by a member of the genus *Streptococcus* in an animal, especially a mammal, most especially a human, comprising administering to said animal such a vaccine, wherein said vaccine is administered in an amount effective to prevent or attenuate said infection. In applying the method of the invention, the transformed microorganism is selected from the group consisting of *Salmonella*, Mycobacteria, *Streptococcus*, poxviruses, and adenoviruses.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The immunogenic fragments of the polypeptide vaccines disclosed according to the invention will include immunogenic fragments of Sp128 (SEQ ID NO:6), which fragments can be readily screened for immunogenic activity, as well as immunogenic fragments of Sp130 (SEQ ID NO: 8). For example, in the amino acid sequence of Sp 130, the fragment corresponding to residues 657 through 773 are known to provide about 40% protection versus the entire Sp130 sequence. Thus, the former fragment protects about 4 out of 10 mice challenged with *Streptococcus pneumoniae* versus 10 of 10 for the entire Sp130 sequence. Thus, specific fragments may include the fragments having amino acid sequences 650–773, 640–773, 630–773, 620–773, 610–773, 600–773, and similar fragments up to the entire Sp130 sequence (SEQ ID NO: 8). It is logical to presume that fragments of Sp128 (SEQ ID NO: 6) may provide similar degrees of protection versus the entire Sp128 protein.

Such variations in homology for putative vaccines are well known in the art (See, for example, Hansen et al., "Active and Passive Immunity Against Borelia bergdorferi Decorin Binding Protein A (DbpA)," *Infection and Immunity*, (May) 1998, p. 2143–2153; Roberts et al., "Heterogeneity Among Genes Including Decorin Binding Proteins A and B of Borelia bergdorferi sensu lato," *Infection and Immunity*, (November) 1998, p. 5275–5285). Such observations would similarly apply to portions of the proteins disclosed herein.

Such fragments or segments find a multitude of uses. For example, such segments of the polypeptides according to the present invention find use as intermediates in the synthesis of higher molecular weight structures also within the present invention.

The term "active fragment" or "immunogenic fragment" means a fragment that generates an immune response (i.e., has immunogenic activity) when administered, alone or optionally with a suitable adjuvant, to an animal, such as a mammal, for example, a rabbit or a mouse, and also including a human.

As noted, the polypeptides, fragments or other derivatives, or analogs thereof, or cells expressing them, can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies, especially where these are in the form of antisera raised against the polypeptides, or fragments thereof, according to the present invention. Such antisera find use in immunization against pneumococcal infection.

Antibodies generated against a polypeptide vaccine corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in *Monoclonal Antibodies and Cancer Therapy*, Alan R. Liss, Inc., pp. 77–96).

Thus, the present invention also relates to the use of the novel polypeptides disclosed herein, as well as to immunogenic fragments thereof, for the production of lymphocytes or hybridoma cells, producing monoclonal antibodies against such polypeptides, or immunogenic fragments thereof. The present invention also relates to the hybridoma cells producing such antibodies.

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples and the like, and for other diagnostic applications.

A vaccine in accordance with the present invention may include one or more of the hereinabove described polypeptides or active fragments thereof. When employing more than one polypeptide or active fragment, such as two or more polypeptides and/or active fragments may be used as a physical mixture or as a fusion of two or more polypeptides or active fragments. The fusion fragment or fusion polypeptide may be produced, for example, by recombinant techniques or by the use of appropriate linkers for fusing previously prepared polypeptides or active fragments.

In many cases, a variation in the polypeptide or active fragment is a conservative amino acid substitution, although other substitutions are within the scope of the invention.

In accordance with the present invention, a polypeptide variant includes variants in which one or more amino acids are substituted and/or deleted and/or inserted.

In another aspect, the invention relates to passive immunity vaccines formulated from antibodies against a polypeptide or active fragment of a polypeptide of the present invention. Such passive immunity vaccines can be utilized to prevent and/or treat pneumococcal infections in patients. In this manner, according to a further aspect of the invention, a vaccine can be produced from a synthetic or recombinant polypeptide of the present invention or an antibody against such polypeptide.

As already described, another aspect the present invention relates to a method of using one or more antibodies (monoclonal, polyclonal or sera) to the polypeptides of the invention as described above for the prophylaxis and/or treatment of diseases that are caused by pneumococcal bacteria. In particular, the invention relates to a method for the prophylaxis and/or treatment of infectious diseases that are caused by *S. pneumoniae*. In a still further preferred aspect, the invention relates to a method for the prophylaxis and/or treatment of otitis media, nasopharyngeal and bronchial infections, and the like in humans by utilizing a vaccine of the present invention.

Generally, vaccines are prepared as injectables, in the form of aqueous solutions or suspensions. Vaccines in an oil base are also well known such as for inhaling. Solid forms which are dissolved or suspended prior to use may also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers may also be used.

Vaccine compositions may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art, or for administration through nasal or respiratory routes.

The amount of vaccine sufficient to confer immunity to pathogenic bacteria is determined by methods well known to those skilled in the art. This quantity will be determined based upon the characteristics of the vaccine recipient and the level of immunity required. Typically, the amount of vaccine to be administered will be determined based upon the judgment of a skilled physician. Where vaccines are administered by subcutaneous or intramuscular injection, a range of 0.5 to 500 µg purified protein may be given.

The present invention is also directed to a vaccine in which a polypeptide or active fragment of the present invention is delivered or administered in the form of a polynucleotide encoding the polypeptide or active fragment, whereby the polypeptide or active fragment is produced in vivo. The polynucleotide may be included in a suitable expression vector and combined with a pharmaceutically acceptable carrier.

In addition, the polypeptides of the present invention can be used as immunogens to stimulate the production of antibodies for use in passive immunotherapy, for use as diagnostic reagents, and for use as reagents in other processes such as affinity chromatography.

In another aspect the present invention provides polynucleotides which encode the hereinabove described polypeptides and active fragments of the invention. The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand.

Host cells are genetically engineered (transduced or transformed or transfected) with the vectors comprising a polynucleotide encoding a polypeptide of the invention. The vector may be, for example, in the form of a plasmid, a viral particle, a phage, etc. The engineered host cells can be cultured in conventional nutrient media modified as appropriate for activating promoters, selecting transformants or amplifying the polynucleotides which encode such polypeptides. The culture conditions, such as temperature, pH and the like, are those previously used with the host cell selected for expression, and will be apparent to the ordinarily skilled artisan.

Vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the proteins.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen, Inc.), pBS, pD10, phagescript, psiX174, pbluescript SK, pBS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacl, lacZ, T3, T7, gpt, lambda $P_R$, $P_L$ and TRP. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice, including streptococcal species, especially S. pneumoniae.

In a further embodiment, microbial organisms genetically transformed with polynucleotides expressing Sp128 or Sp130, or both, may themselves be used as living vaccine delivery vehicles. Examples include, but are in no way limited to, Salmonella species, Mycobacterium species, Streptococcus species, poxviruses, adenoviruses, and the like. In addition, transgenic edible plants may also be candidates for vaccine delivery.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Amersham Pharmacia Biotech, Piscataway, N.J., USA) and pGEM1 (Promega, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, a french press, mechanical disruption, or use of cell lysing agents, such methods are well know to those skilled in the art. However, preferred are host cells which secrete the polypeptide of the invention and permit recovery of the polypeptide from the culture media.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and/or purified from recombinant cell cultures by well-known protein recovery and purification methods. Such methodology may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. In this respect, chaperones may be used in such a refolding procedure. Finally, high performance liquid chromatography (HPLC) can be employed for final purification steps.

The polypeptides that are useful as immunogens in the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

Procedures for the isolation of the individually expressed polypeptides may be isolated by recombinant expression/isolation methods that are well-known in the art. Typical examples for such isolation may utilize an antibody to a conserved area of the protein or to a His tag or cleavable leader or tail that is expressed as part of the protein structure.

Specific embodiments of the invention will now be further described in more detail in the following non-limiting examples and it will be appreciated that additional and different embodiments of the teachings of the present invention will doubtless suggest themselves to those of skill in the art and such other embodiments are considered to have been inferred from the disclosure herein.

EXAMPLE 1

Active Protection with Anti-Sp128 and Anti-Sp130

A. Cloning, Expression, and Purification of Sp128 and Sp130

The genomic DNA used as target for amplification using the polymerase chain reaction was isolated from *Streptococcus pneumoniae* (Norway strain—serotype 4), the same strain used for genomic sequencing. The nucleotide sequence of the gene fragments encoding Sp128 (SEQ ID NO: 5) and Sp130 (SEQ ID NO: 7) with the corresponding amino acid sequence for polypeptides Sp128 (SEQ ID NO: 6) and Sp130 (SEQ ID NO: 8) are provided in the Sequence Listing.

Primers (SEQ ID NOS: 1–4) were designed so as to amplify either Sp128 or Sp130 gene fragments and allow their cloning into the *E. coli* expresssion vector pQE10 with, for example, subsequent expression of a histidine-tagged protein product for purification by Nickel-affinity chromatography.

Thus, cloning of the fragments amplified by the primers of SEQ ID NOS: 1 and 2 results in the polypeptide of SEQ ID NO: 6 (denoted Sp128), while cloning of the fragment amplified using the primers disclosed in SEQ ID NOS: 3 and 4 result in the polypeptide of SEQ ID NO: 8 (denoted Sp130).

B. Vaccination with Sp128 and Sp130 Results in Protection Against Lethal *S. pneumoniae* Challenge In each of the experiments shown in FIG. 1, C3H/HeJ mice (10 per group) were immunized intraperitoneally (i.p.) with either Sp128 or Sp130 protein (15 µg in 50 µl PBS (phosphate buffered saline) emulsified in 50 µl complete Freund's adjuvant (CFA)). A group of 10 mice were sham-immunized with PBS and CFA only.

A second immunization of 15 µg protein with incomplete Freund's adjuvant (IFA) was administered 3 weeks later (with the sham-immunized group receiving PBS and IFA).

Blood was drawn (retro-orbital bleed) at week 7. Sera from each group were pooled for analysis of anti-Sp128 and anti-Sp130 antibody by ELISA. Mice were challenged at week 8 by intraperitoneal injection of approximately 400 CFU (colony forming units) of *S. pneumoniae* strain SJ2 (capsular serotype 6B). In preliminary experiments, the median infection dose ($LD_{50}$) of this strain was determined to be approximately 10 CFU. Mice were monitored for 14 days of survival.

Figure 1:
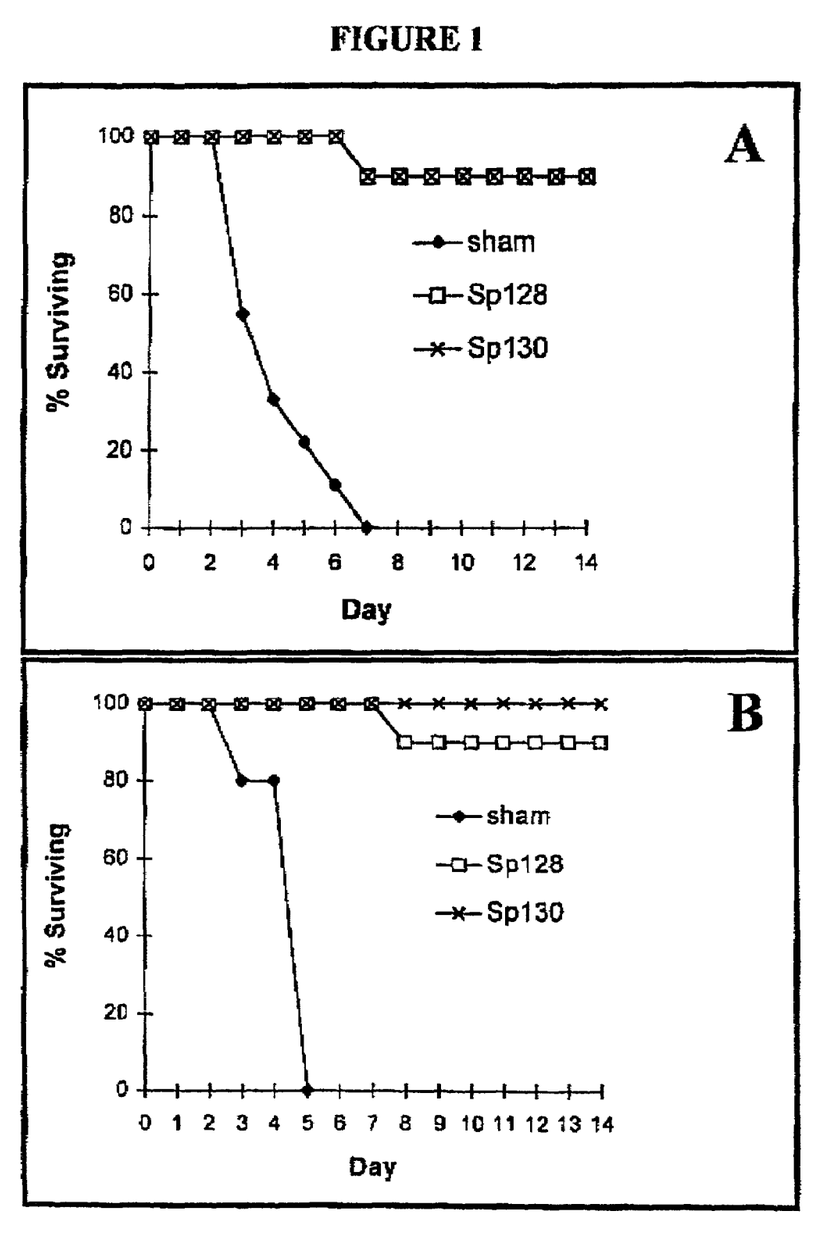

Both experiments shown in FIG. 1 used the same preparations of recombinant Sp128 and Sp130.

In the experiment shown in FIG. 1A, 7-week serum collected from the 10 mice immunized with either Sp128 or Sp130 each had an endpoint ELISA titer of 1:2,048,000 and 1:1,024,000, respectively. No anti-Sp128 or anti-Sp130 antibody was detected in sera from sham-imunized mice. Ninety percent of the mice immunized with either Sp128 or Sp130 protein survived the challenge (406 CFU of pneumococci) for the extent of the study (14 days). One hundred percent of sham-immunized mice were dead by day 7.

In the experiment shown in FIG. 1B, 7-week sera collected from the 10 mice immunized with either Sp128 or Sp130 each had an endpoint ELISA titer of 1:1,024,000 and 1:512,000, respectively. No anti-Sp128 or anti-Sp130 antibody was detected in sera from sham-imunized mice. Ninety and one hundred percent of the mice immunized with either Sp128 or Sp130 protein, respectively, survived the challenge (404 CFU of pneumococci) for the extent of the study (14 days). One hundred percent of sham-immunized mice were dead by day 5.

These data indicate that immunization of mice with either recombinant Sp128 or Sp130 proteins elicit a response capable of protecting against systemic pneumococcal infection and subsequent death. Cross protection is demonstrated by the fact that the recombinant pneumococcal protein was generated based on capsular serotype 4 DNA sequence, while the challenge was with the heterologous strain SJ2 (capsular serotype 6B).

EXAMPLE 2

Passive Protection with Anti-Sp130 Antisera

A. Generation of Rabbit Immune Sera

Following collection of pre-immune serum, a New Zealand White rabbit was immunized with 250 µg of Sp130 (SEQ ID NO:8) in complete Freund's adjuvant. The rabbit was given 2 boosts of 125 µg Sp130 in incomplete Freund's adjuvant on days 21 and 52, and bled on days 31 and 62.

B. Passive Protection in Mice

Figure 2:
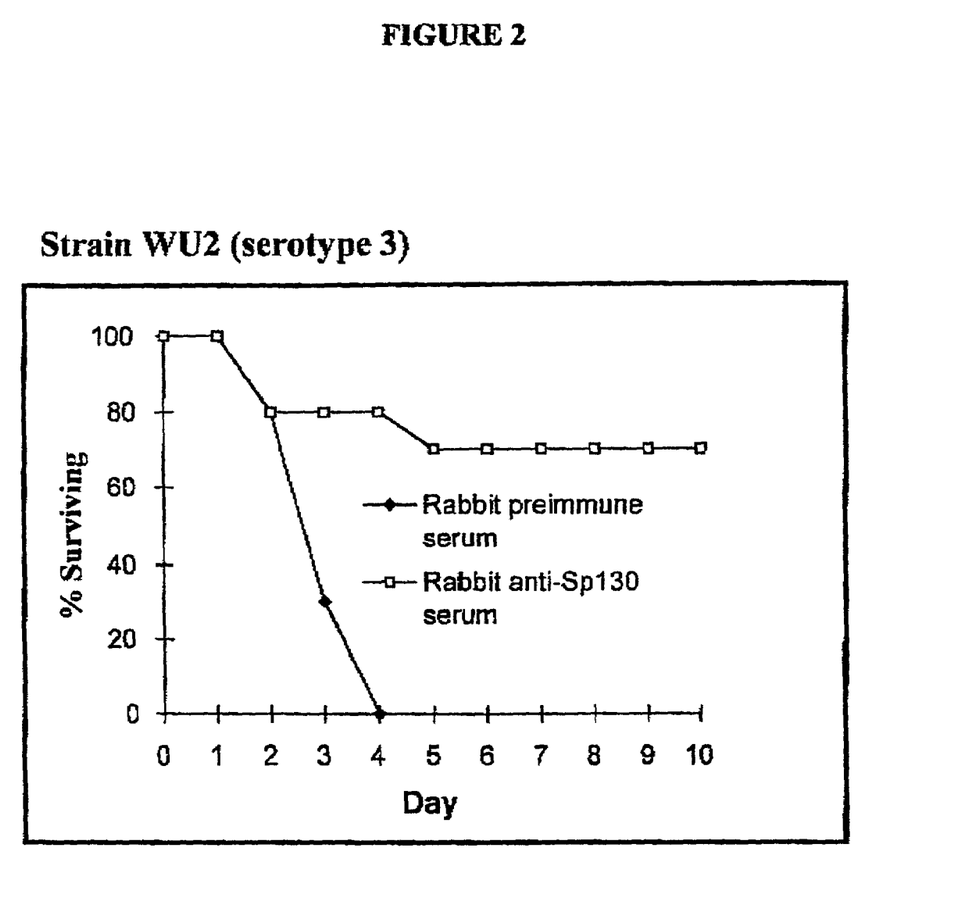
FIG. 2 shows the results of passive administration of rabbit antiserum raised against Sp130 derived from Norway serotype 4. Such administration was able to protect mice in the pneumococcal sepsis model using a heterologous strain. More specifically, 70% of the mice immunized with the Sp130 antiserum survived the 10 day observation period after challenge with 1400 CFU of strain WU2 (serotype 3). In addition, 100% of the mice immunized with a control serum (collected before immunization) died by day 4.

BALB/cByJ mice (10 per group) were passively immunized by 2 i.p. injections of 100 µl of rabbit serum. The first injection was administered 24 hours before challenge with 1400 CFU of *S. pneumoniae* strain WU2, and the second injection was given 4 hours after challenge. FIG. 2 shows the survival of mice after infection with WU2 (capsular serotype 3) strain. In preliminary experiments, the $LD_{50}$ of this strain was determined to be approximately 100 CFU.

FIG. 2 shows the survival of mice injected with 1400 CFU of strain WU2. As shown therein, 70% of the mice immunized with rabbit immune serum raised against Sp130 protein survived the 10 day observation period. Of the mice immunized with the control serum (collected from a rabbit prior to immunization), 100% died by day 4.

These data suggest that the protection against pneumococcal infection resulting from immunization with Sp130 is antibody-mediated, since the mice were protected by passive transfer of serum from a hyperimmunized rabbit. As seen in the previously described mouse active challenge experiments, serum directed against recombinant Sp130 protein cloned from a serotype 4 strain was protective against challenge with a heterologous strain, WU2 (capsular serotype 3).

EXAMPLE 3

Conservation of Sp128-Sp130 Among Strains of *S. pneumoniae*

A. Western Blotting

The pneumococcal strains used in this experiment were obtained from the American Type Culture Collection (10801 University Boulevard, Manassas, Va. 20110-2209) and include one isolate from each of the serotypes in the currently used multivalent pneumococcal vaccine.

For total cell lysates, pneumocci were grown to mid-logarithmic phase (absorbance at 620 nm was 0.4 to 0.6) in 2 ml Todd-Hewitt broth with 5% yeast extract (from Difco, Detroit, Mich.) at 37° C. Bacteria were harvested by centrifugation and washed twice with water. Pellets (consisting of sedimented cells) were resuspended in 200 µl of lysis buffer (0.01% sodium dodecyl sulfate, 0.15 M sodium citrate, and 0.1% sodium deoxycholate) and incubated at 37°

C. for 30 min, then diluted in an equal volume of 2×SSC (0.3 M NaCl, 0.03 M sodium citrate). Polypeptides in the lysates were resolved on SDS-PAGE (sodium dodecyl sulfate polyacrylamide gel electrophoresis), transferred to nitrocellulose membranes (Bio-Rad Laboratories, Hercules, Calif.) and probed with antibody by conventional Western Blotting procedures. Sera from a New Zealand White rabbit immunized with Sp130 (as per Example 2, supra) was used at a dilution of 1:3000. Bound antibody was detected with peroxidase-conjugated sheep anti-rabbit IgG using a chemiluminescence kit from Amersham Inc. (Cambridge, Mass.).

Figure 3:
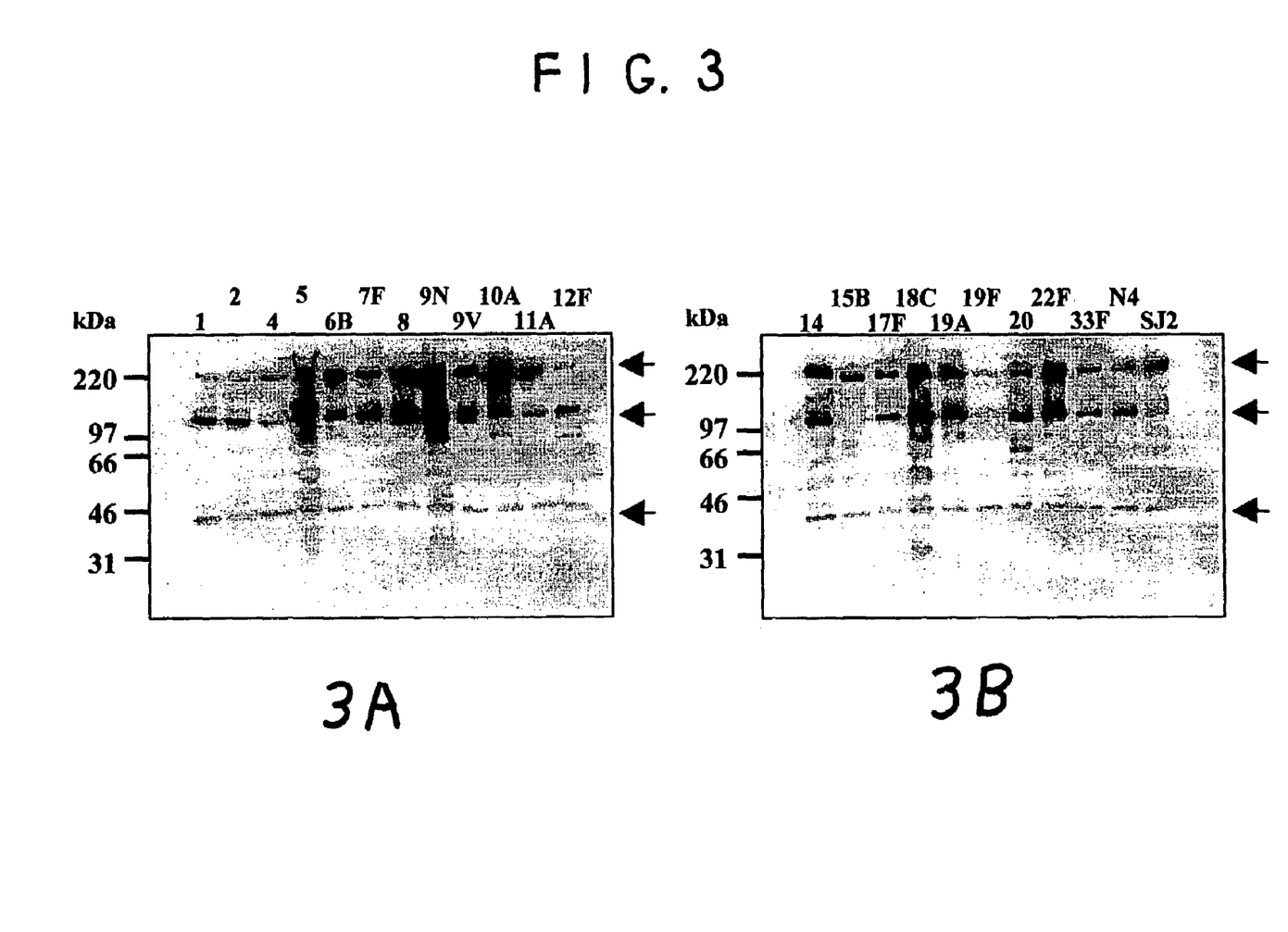
FIGS. 3A and 3B are western blots showing reactivity of antisera raised against recombinant Sp130 (derived from strain Norway serotype 4) with whole cell lysates of heterologous stains. All *S. pneumoniae* strains tested showed a band of molecular weight about 220 kD, the expected mass for a protein containing both the Sp 128 and Sp130 sequences, indicating that this protein was present in all the tested strains. Tested strains included isolates from each of the pneumococcal serotypes represented in the currently used 23-valent polysaccharide vaccine.

The rabbit anti-Sp130 sera revealed 2 major bands with apparent molecular weights of 110 kD and 220 kD in all 23 pneumococcal lysates tested (as shown in FIGS. 3A and 3B).

These data show that Sp130 is expressed and shares common antigenic epitopes among strains of the 23 pneumococcal capsular serotypes represented in the currently used polysaccharide vaccine.

EXAMPLE 4

Immunogenicity of Sp128 and Sp130 in Humans

Sera from patients with culture-proven pneumococcal bacteremia were used in Western blots containing recombinant Sp128 or Sp130 protein. In the experiment shown in FIG. 4, sera from 5 patients (indicated by numerals 1 through 5) were diluted 1:3000 and used to probe blots containing Sp128 (SEQ ID NO:6) or Sp130 (SEQ ID NO:8).

Figure 4:
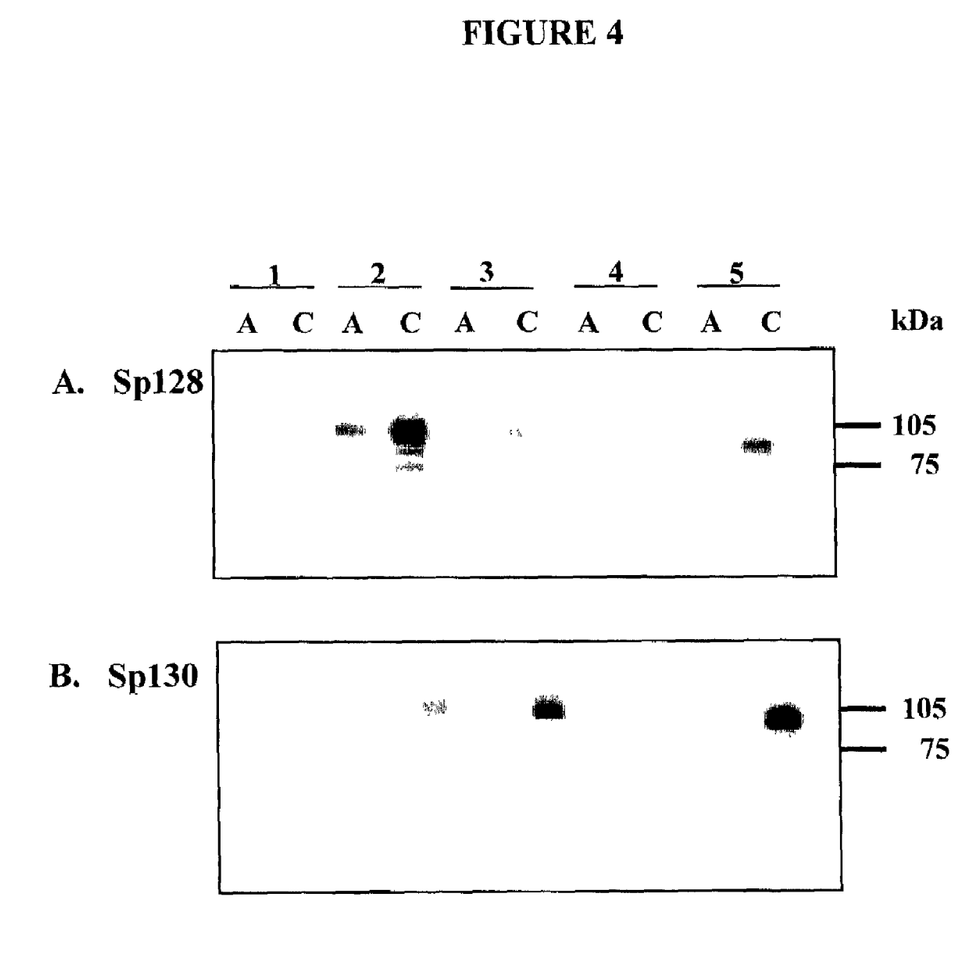
FIG. 4 is a western blot showing the reactivity of patient sera with either Sp128 or Sp130.

The lanes labeled "A" (for "acute") were probed with serum collected shortly after diagnosis of pneumococcal infection; lanes denoted "C" (for "convalescent") were probed with serum collected either 1 month later (patients 1, 2, and 3) or 8 days after the first serum collection (patients 4 and 5). For patients 2, 3, and 5, reactivity of the convalescent serum with Sp128 and Sp130 was stronger than that of the corresponding acute serum.

Other experiments (not depicted in the figure) showed that convalescent sera from 17 patients with pneumococcal infections were tested individually for reactivity with either Sp128 or Sp130. Thus, 10 and 15 of the 23 sera were found to bind (on a Western Blot) Sp128 and Sp130, respectively.

These experiments indicate that Sp128 and Sp130 (the latter to a greater extent), are recognized by the human immune system and suggest that antibodies able to bind the Sp128-Sp130 protein may be produced during natural *S. pneumoniae* infection in humans. Further, this provides indirect evidence that Sp128 and Sp130 are expressed in vivo by *S. pneumoniae* during this phase of infection, and thus may be available as targets for immunoprophylaxis, immunotherapy, or to provide anamnestic immune responses in subjects vaccinated with these proteins. Since the patients were infected with a variety of pneumococcal strains, these data also support the idea that Sp130 is more antigenically conserved than Sp128.

What is claimed is:

1. An immunogenic composition comprising an isolated polypeptide comprising the amino acid sequence of SEQ ID NO: 8.

2. A vaccine comprising the immunogenic composition of claim 1 and a pharmaceutically acceptable carrier, wherein said polypeptide is present in an amount effective to elicit protective antibodies in a mammal against *Streptococcus pneumoniae*.

3. A method of attenuating an infection caused by *Streptococcus pneumoniae* in a mammal comprising administering to said mammal the immunogenic composition of claim 1 comprising the polypeptide in an amount effective to attenuate said *Streptococcus pneumoniae* infection.

4. A method of immunizing a mammal against an infection caused by *Streptococcus pneumoniae* comprising administering to said mammal the vaccine of claim 2.

5. An immunogenic composition comprising one or more immunogenic fragments selected from the group consisting of amino acid residues 650–773, 640–773, 630–773, 620–773, 610–773, and 600–773 of the amino acid sequence of SEQ ID NO: 8.

6. A method of immunizing a mammal against an infection caused by *Streptococcus pneumoniae* comprising administering to said mammal the immunogenic composition of claim 5.

* * * * *